United States Patent [19]

Imran et al.

[11] Patent Number: 5,520,645
[45] Date of Patent: May 28, 1996

[54] LOW PROFILE ANGIOPLASTY CATHETER AND/OR GUIDE WIRE AND METHOD

[75] Inventors: Mir A. Imran, Palo Alto; Deepak R. Gandhi, San Jose; Dennis L. Brooks, Santa Clara, all of Calif.

[73] Assignee: Intelliwire, Inc., Sunnyvale, Calif.

[21] Appl. No.: 331,217

[22] Filed: Oct. 28, 1994

[51] Int. Cl.[6] .................................................. A61M 37/00
[52] U.S. Cl. ......................... 604/95; 604/96; 604/103
[58] Field of Search .............................. 604/95, 96, 97, 604/98, 103, 104; 600/146, 152

[56] References Cited

U.S. PATENT DOCUMENTS

| | | | |
|---|---|---|---|
| 4,664,113 | 5/1987 | Frisbie et al. | 604/96 |
| 4,793,350 | 12/1988 | Mar et al. | 604/96 |
| 4,838,269 | 6/1989 | Robinson et al. | 604/96 |
| 4,846,174 | 7/1989 | Willard et al. | 604/95 |
| 4,848,344 | 7/1989 | Sos et al. | 606/194 |
| 5,035,694 | 7/1991 | Kasprzyk et al. | 604/96 |
| 5,045,061 | 9/1991 | Seifert et al. | 604/96 |
| 5,255,690 | 10/1993 | Keith et al. | 604/96 |
| 5,338,301 | 8/1994 | Diaz et al. | |
| 5,349,964 | 9/1994 | Imran et al. | 604/95 |
| 5,364,354 | 11/1994 | Walker et al. | 604/96 |
| 5,378,236 | 1/1995 | Seifert | 606/194 |

*Primary Examiner*—Corrine M. McDermott
*Assistant Examiner*—N. Kent Gring
*Attorney, Agent, or Firm*—Flehr, Hohbach, Test, Albritton & Herbert

[57] ABSTRACT

A low profile balloon-on-a-wire catheter having a flexible elongate tubular member with proximal and distal extremities and with a lumen extending from the proximal extremity to the distal extremity. An inflatable balloon is mounted on the distal extremity of the flexible elongate tubular member. Communication is established between the lumen and the interior of the inflatable balloon. An inflation fitting is removably secured to the proximal extremity of the flexible elongate tubular member for supplying an inflation fluid to the lumen for inflating and deflating the balloon. The inflation fitting when removed provides a proximal extremity on the catheter which is free of obstructions so that another balloon catheter can be advanced over the proximal extremity of the flexible elongate tubular member.

6 Claims, 2 Drawing Sheets

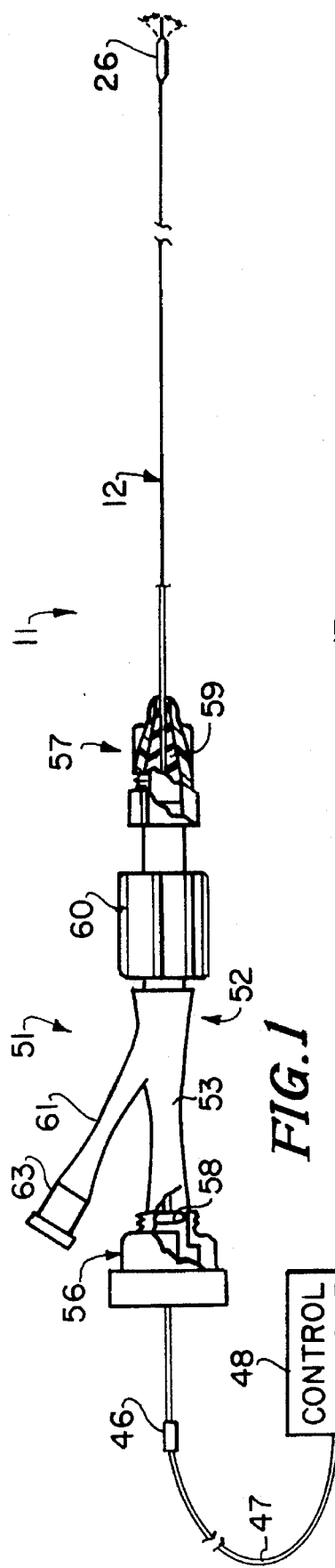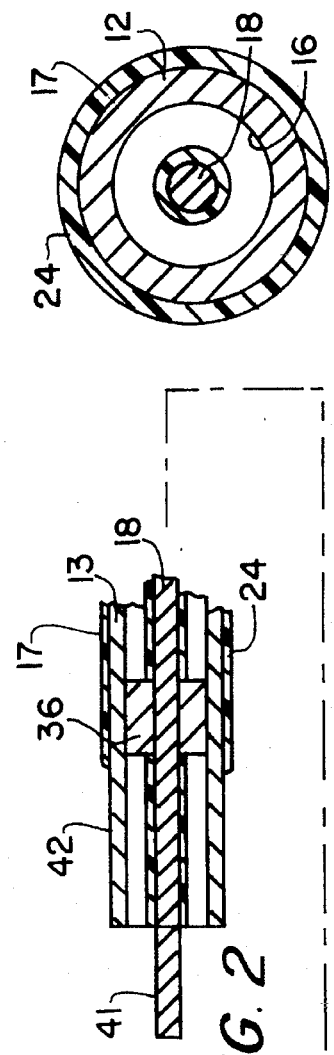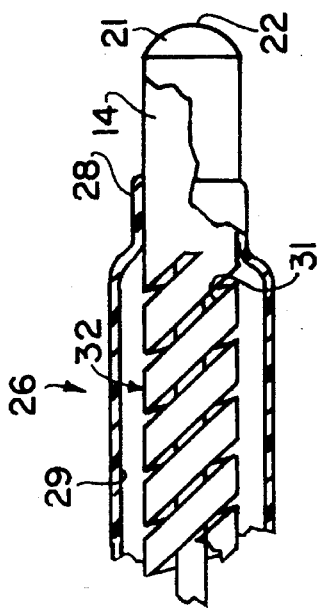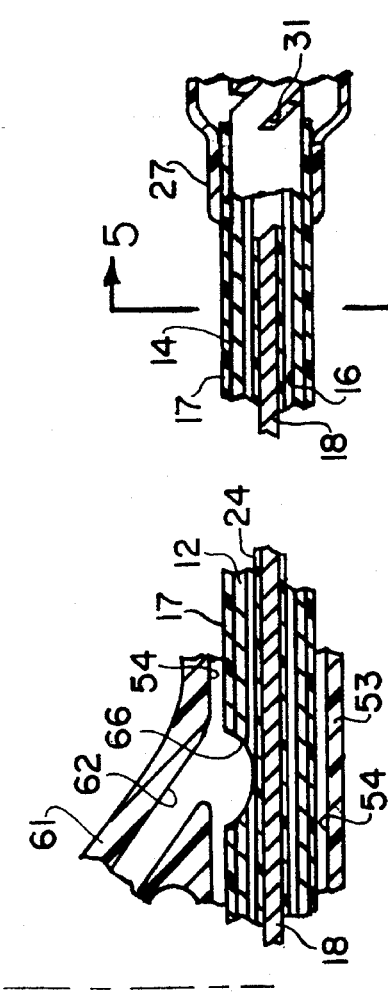

LOW PROFILE ANGIOPLASTY CATHETER AND/OR GUIDE WIRE AND METHOD

This invention relates to a low profile balloon-on-a-wire catheter which also may be characterized as a fixed wire balloon on-a-wire catheter with removable attachments on the proximal extremity so that the balloon on-a-wire catheter can be utilized as an independent stand-alone guide wire.

Balloon-on-wire catheters have heretofore been provided. Typically however such balloon-on-a-wire catheters have been provided with attachments on their proximal extremities which are not removable limiting the balloon-on-a-wire catheter to a single use. This requires that the balloon on-a-wire catheter be removed if it is desired to utilize a larger size balloon during an angioplasty procedure. There is therefore need for a new and improved balloon-on-a-wire catheter which can be utilized as an independent stand-alone guide wire.

In general, it is an object of the present invention to provide a low profile balloon-on-a-wire catheter in which attachments carried by the proximal extremity can be removed so that the catheter can be utilized as an independent stand-alone guide wire.

Another object of the invention is to provide a catheter of the above character in which the distal extremity can be steered.

Another object of the invention is to provide a catheter of the above character in which a removable attachment is provided on the proximal extremity of the catheter for inflating and deflating the balloon.

Another object of the invention is to provide a catheter of the above character in which an attachment is provided for making electrical connections to the proximal extremity of the catheter for steering the distal extremity of the catheter.

Another object of the invention is to provide a catheter of the above character which can be utilized as a small diameter stand-alone guide wire.

Another object of the invention is to provide a catheter of the above character in which the catheter can be utilized in a rapid exchange.

Another object of the invention is to provide a catheter of the above character which when used as an independent stand-alone guide wire so that larger size angioplasty balloon catheters can be advanced over the stand-alone guide wire.

Additional objects and features of the invention will appear from the following description in which the preferred embodiments are set forth in detail in conjunction with the accompanying drawings.

FIG. 1 is a side elevational view of a low profile balloon-on-a-wire catheter incorporating the present invention.

FIG. 2 is an enlarged cross-sectional view of the proximal extremity of the catheter shown in FIG. 1.

FIG. 3 is an enlarged cross sectional view of an intermediate portion of the catheter shown in FIG. 1.

FIG. 4 is an enlarged sectional view of the distal extremity of the catheter shown in FIG. 1.

FIG. 5 is a cross sectional view taken along the line of 5—5 of FIG. 4.

Figure 6:
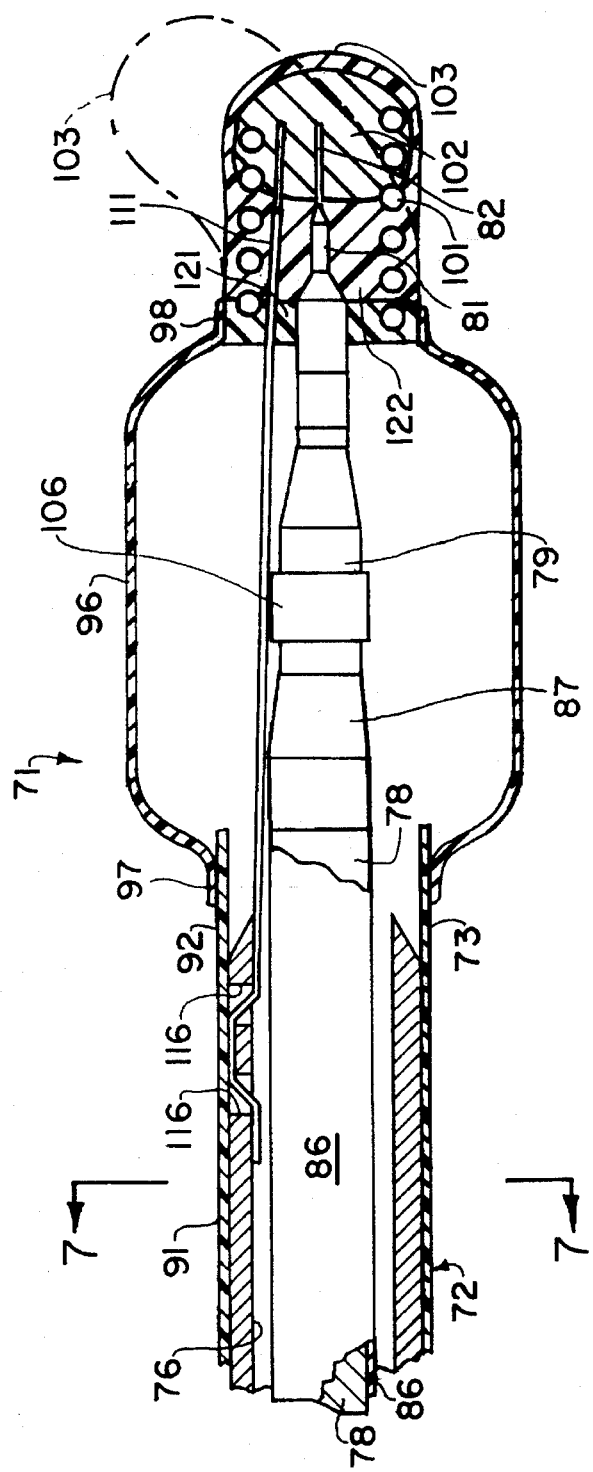
FIG. 6 is an enlarged sectional view of the distal extremity of a balloon-on-a-wire catheter incorporating another embodiment of the present invention.

In general, the low profile balloon-on-a-wire catheter is comprised of a flexible elongate tubular member having proximal and distal extremities and having a lumen extending from the proximal extremity to the distal extremity. An inflatable balloon is carried by the distal extremity. Means is carried by the flexible elongate tubular member for establishing communication between the lumen and the interior of the inflatable balloon. An inflation connector is removably secured to the proximal extremity of the flexible elongate tubular member for supplying an inflation fluid to the lumen for inflating and deflating the balloon. The inflation connector when removed provides a proximal extremity for the flexible elongate tubular member which is free of obstructions so that the flexible elongate tubular member can serve as a guide wire for permitting advancement of another balloon angioplasty catheter over the flexible elongate tubular member so that the flexible elongate tubular member can serve as a stand-alone guide wire.

An electrical device is provided in the distal extremity of the flexible elongate tubular member. Conductive means is provided in the flexible elongate tubular member and is connected to the electrical device and extends to the proximal extremity. Removable connector means is coupled to the proximal extremity of the flexible elongate tubular member and makes electrical contact with the conductive means. The removable connector means when removed from the flexible elongate tubular member provides a proximal extremity on the flexible elongate tubular member which is free of obstructions so that another angioplasty catheter can be advanced over the flexible elongate tubular member utilizing the flexible elongate tubular member as a stand alone guide wire.

More in particular as shown in FIGS. 1 through 5 of the drawings, the low profile balloon on-a-wire catheter 11 consists of a flexible elongate tubular member 12 having proximal and distal extremities 13 and 14 and having a lumen 16 extending from the proximal extremity 13 to the distal extremity 14. The flexible elongate tubular member 12 can be of a suitable material. For example it can be formed of stainless steel having an outside diameter ranging from 0.010" to 0.032" but in accordance with the present invention preferably has a size ranging from 0.014" to 0.018" in outside diameter. Such a stainless steel hypotube can have a wall thickness of 0.003" which for a 0.018" flexible elongate member would provide a lumen 16 of 0.012" in diameter. An insulating layer 17 formed of a suitable material such as a polyimide extends over the outer surface of the elongate tubular member 12.

A mandrel or core wire 18 is disposed within the lumen 16 of the flexible elongate tubular member 12 and can also be formed of a suitable material such as stainless steel. The core wire or mandrel 18 can have a suitable diameter such as 0.008" so that there remains a coaxial or annular space which can serve as the lumen for inflating and deflating the balloon as hereinafter described. As shown in FIGS. 1 through 5, the core wire 18 can extend from the proximal extremity to the distal extremity of the catheter 11. Typically such a mandrel or core wire 18 would have centerless ground portions of reduced diameter to impart additional flexibility to the distal extremity of the catheter as described in the embodiment of the present invention shown in FIGS. 6 and 7. The distal extremity can be flattened to provide a ribbon-like configuration which is bonded into a solder bead or weld 21 in the form of a ball to provide a hemispherical frontal surface 22. This ball 21 secures the mandrel or core wire 18 to the distal extremity of the flexible elongate tubular member 12.

In order that the mandrel or core wire 18 can be utilized as an electrical conductor, a layer of insulation 24 of a suitable material such as a polyimide of a suitable thickness as for example 0.001" is provided.

An elongate balloon 26 formed of a non-elastomeric material is bonded to the distal extremity of the flexible elongate tubular member 12. The proximal and distal extremities 27 and 28 of the balloon are bonded to the distal extremity 14 of the flexible elongate tubular member 12 by suitable means such an adhesive so that a fluid-tight seal is formed between the proximal and distal extremities 27 and 28 and the flexible elongate member 12. The balloon 26 typically would have an inflated diameter of 1.0 to 4.0 millimeters. Such a balloon would have a wall thickness range of 0.0005" to 0.002" and would have a suitable length as for example 2 to 3 centimeters.

Means is provided for establishing communication between the lumen 16 of the flexible elongate tubular member 12 and the interior 29 of the balloon 26 and consists of a spiral slot 31 extending through the wall of the hypotube forming the flexible elongate tubular member 12 as shown in FIG. 4. The slot 31 causes a helix 32 to be formed in the distal extremity of the hypotube 12. In addition to providing a means for establishing communication between the lumen 16 and the interior 29 of the balloon 26, the helix 32 serves to impart additional flexibility to the distal extremity of the flexible elongate tubular member 12 to facilitate steering and bending of the same. It should be appreciated that the helix 32 can be formed as a separate part and then be bonded by suitable means such as welding to the flexible elongate tubular member 12. Alternatively, the helix 32 can be formed in the distal extremity 14 of the flexible elongate tubular member 12. The other or proximal end of the lumen 16 is sealed in a suitable manner such as by an epoxy seal 36 (see FIG. 2) disposed about the inside core wire 18.

Figure 7:
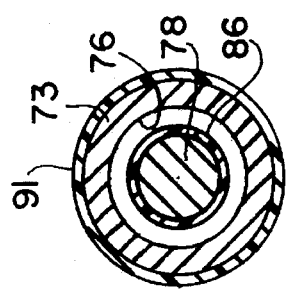
FIG. 7 is a cross sectional view taken along the line 7—7 of FIG. 6.

An electrical device (not shown) of the type described in U.S. Pat. No. 5,238,005 and as shown in FIGS. 6 and 7 of another embodiment of the present invention utilizes a Nitinol element (not shown) disposed within the helix 32 is provided for steering or bending the distal extremity 14 of the flexible elongate tubular member 12 as indicated by the dash lines shown in FIG. 1. Conductive means is provided for supplying electrical current to the electrical device and in the present embodiment of the invention this conductive means is provided by the insulated core wire or mandrel 18 serving as one conductor and the hypotube 12 forming the flexible elongate tubular member 12 serving as the second conductor to provide conductive means which extends to the proximal extremity 13. The uninsulated portion of the core wire or mandrel 18 serves to provide one cylindrical contact 41 and the uninsulated portion of the flexible elongate tubular member 12 in the form of the hypotube serves as the second cylindrical contact 42. These coaxial contacts 41 and 42 are adapted to be engaged by a conventional removable connector 46 which is connected by cable 47 to a control console 48. The control console supplies electrical power to the electrical device provided in the distal extremity for causing the desired bending of the distal extremity 14 of the flexible elongate member 12. The connector 46 when removed from the proximal extremity of the flexible elongate tubular member 12 provides a proximal extremity for the flexible elongate tubular member which is free of obstructions so that another catheter can be advanced over the flexible elongate tubular member 12 permitting the flexible elongate tubular member 12 forming the catheter to be utilized as a stand alone guide wire as hereinafter described.

Removable inflation means 51 is secured to the proximal extremity of the flexible elongate member 12 and consists of a conventional Tuohy Borst adapter 52. This adapter consists of a tubular member 53 formed of suitable material such as a clear plastic which is provided with a flow passage 54 therein through which the flexible elongate tubular member 12 can extend as shown particularly in FIGS. 1 and 3. Adjustable seal assemblies 56 and 57 having respectively seals 58 and 59 therein are provided on opposite ends of the tubular member 53 and are adapted to be moved into frictional engagement with the flexible elongate element 12 to establish fluid-tight high pressure seals therewith. A torquer 60 is disposed between the seal assemblies 56 and 57 and adapted to be engaged by the fingers of the hand for rotating the distal extremity of the catheter and/or guide wire 12. The proximal seal assembly 56 is loosened slightly to permit rotation of the flexible elongate tubular member within the seal 58 while retaining a fluid-tight seal therewith.

The tubular member 53 is provided with a leg 61 which branches off at an angle from the flow passage 54. It is provided with a flow passage 62 in communication with the flow passage 54 and in communication with the conventional Luer fitting 63 which is adapted to receive a syringe that can be utilized for introducing an inflation fluid in the form of a radiopaque dye or a saline solution into the passage 62 and into the passage 54 so that the inflating fluid can be introduced into the lumen 16 of the flexible elongate member 12. Means is provided for establishing communication between the passage 54 and the lumen 16 of the flexible elongate tubular member and consists of one or more elongate slots 66 formed in the sidewall of the hypotube forming the flexible elongate tubular member 12.

It can be seen that the inflation means 51 can be readily removed from the proximal extremity of the flexible elongate tubular member 12 by releasing the O-ring seal assemblies 56 and 57 from the flexible elongate tubular member 12 and then slipping the inflation means in the form of a Tuohy Borst adapter 52 or connector off of the proximal extremity of the flexible elongate tubular member 12 to provide a proximal extremity on the flexible elongate tubular member 12 which is free of obstructions so that another angioplasty catheter can be advanced over the flexible elongate tubular member utilizing the flexible elongate tubular member as a stand alone guide wire.

In connection with the present invention it should be appreciated that the core wire or mandrel if desired can be provided of a reduced length as of example extending only approximately 30 centimeters from the distal extremity of the catheter 11 typically having a length of 150 to 180 centimeters. In such an embodiment, the conductive means would take the form of at least one additional wire and possible two additional wires connected to the electrical device in the distal extremity of the flexible elongate tubular member 12 and extending to the proximal extremity where they can be secured to conductive slip rings (not shown) to form the electrical connection with the connector 46.

Operation and use of the low profile balloon on-a-wire catheter may now be described as follows. Let it be assumed that an angioplasty procedure is to be performed on a patient who has a stenosis or as occlusion which almost completely blocks an arterial vessel. For that reason it normally is desirable to utilize a very low profile balloon-on-a-wire catheter such as disclosed in the present invention. Before commencement of the procedure, the inflation adapter 51 and the connector 46 would typically be placed on the proximal extremity of the catheter 11. A guiding catheter is introduced into the femoral artery in a conventional manner after which the low profile balloon-on-a-wire catheter 11 incorporating the present invention is introduced into the guiding catheter and then into the vessel by steering the same with the use of the torquer 60 through any tortuosities which may be encountered in the vessel until the stenosis is reached. The progress of the distal extremity of the low profile balloon-on-a-wire catheter can be observed fluoroscopically in a manner well known to those skilled in the art. The catheter 11 is then advanced through the stenosis until the balloon 26 is in registration with the stenosis.

After the balloon 26 has been positioned within the stenosis, the balloon 26 can be inflated by supplying an inflation fluid as for example by a syringe to the adapter 51 so that the fluid will pass to the lumen 16 of the flexible elongate member 12 and then in to the interior 29 of the balloon 26. The balloon 26 can be inflated and deflated one or more times as desired by the physician to create an opening in the stenosis which is at least large enough to permit some blood to flow through the stenosis.

Let it be assumed that it is desired to still further expand the opening through the stenosis by the use of an additional balloon-on-a-wire catheter of a conventional type having a size balloon. When this is to be done, the connector 46 is removed and the balloon 26 is deflated after which the adapter 51 is removed by slipping it off of the proximal extremity of the flexible elongate member 12. This can be readily accomplished by merely loosening the seal 56 and 57 from the elongate tubular member 12 and slipping it off of the flexible elongate member 12.

The catheter 11 which remains in place can have an outside diameter of approximately that of the main body of the catheter. Thus, in the embodiment shown in FIGS. 1–5 the balloon 26 when deflated would only have a nominal wall thickness of 0.0005" so that when the balloon 26 is deflated the distal extremity of the catheter has an overall diameter which is approximately equal to or less than the diameter of the catheter 11 as for example 0.018". A conventional balloon catheter can then be introduced over the catheter 11 utilizing the catheter 11 as a stand-alone guide wire to guide the larger size balloon angioplasty catheter into the stenosis. If desired, the catheter 11 of the present invention can be left in a position with the deflated balloon 26 thereon in registration with the stenosis. The other balloon of the conventional balloon catheter then can be moved over the deflated balloon 26. Alternatively, the catheter 11 with the deflated balloon 26 thereon can be advanced distally beyond the stenosis. The conventional balloon catheter can then be advanced over the catheter 11 until its balloon is in registration with the stenosis. The balloon carried by the conventional balloon catheter can then be inflated and deflated one or more times as desired by the physician to additionally dilate the stenosis to thereby create increased blood flow through the stenosis. If desired, the conventional balloon catheter can be removed leaving the catheter 11 of the present invention still in place and then advancing a still larger size conventional balloon catheter over the catheter and utilizing the same inflation and deflation procedure until the desired dilation of the stenosis has been obtained.

In connection with the use of the catheter 11 of the present invention, it should be appreciated that a conventional rapid exchange catheter can be utilized in connection with the catheter 11 if desired.

Another embodiment of a low profile balloon-on-a-wire catheter incorporating the present invention is disclosed in FIGS. 6 and 7. The balloon-on-a-wire catheter 71 shown therein consists of a flexible elongate tubular member 72 which has a proximal extremity (not shown) and a distal extremity 73. The flexible elongate tubular member 72 can be formed of a suitable material such as a stainless steel hypotube having an outside diameter of 0.018" and having a wall thickness of 0.002" to provide a balloon inflation lumen 76 extending from the proximal extremity (not shown) to the distal extremity 73. A core wire or mandrel 78 is disposed within the lumen 76 and is formed of a suitable material such as stainless steel. It can be of a suitable diameter as for example 0.006" to 0.008". The distal extremity of the core wire or mandrel 78 is provided with a portion 79 of reduced or smaller diameter as for example 0.004", another portion 81 of a still smaller diameter as for example 0.003" and a flattened rectangular ribbon-like portion 82. The core wire 78 is coated with an insulating coating 86 of a suitable material such as a polyimide to a thickness of approximately 0.0005". The distal extremity of the flexible elongate tubular member 72 is swaged inwardly or ground down at 87.

A sleeve or elongate tubular member 91 is provided which extends the length of the flexible elongate tubular member 72 and is formed of a suitable material such as a polyimide. It has an outside diameter as for example of 0.018" and a wall thickness of 0.002".

A balloon 96 formed of a typical non-elastomeric material such as polyethylene or PET has its proximal extremity 97 bonded to the exterior of the sleeve 91 by suitable means such as an adhesive. The distal extremity 98 of the balloon 96 is also bonded to the distal extremity of the sleeve 91 by suitable means such as an adhesive. A coil spring 101 is formed of a radiopaque suitable material such as a platinum tungsten alloy. Its proximal extremity is sealed within the distal extremity of the sleeve 91 by suitable means such as an adhesive 102. The distal extremity of the spring 101 is secured to the core wire or mandrel 78 and to the sleeve by a TEG weld forming a ball 102 providing a hemispheric forwardly or distally facing surface 103. A radiopaque marker 106 formed of a suitable material such as gold or platinum is disposed within the interior of the balloon 96 equidistant from the ends thereof on the exterior surface of the sleeve 91.

Suitable steering means of the type disclosed in U.S. Pat. No. 5,238,005 is provided to permit steering of the distal extremity of the catheter or guide wire 71 as shown by dotted lines in FIG. 6 of the coil spring 101. This steering means consists of a Nitinol actuator wire or ribbon 111 having one end embedded in the ball 102 and having the other end secured to the distal extremity of the flexible elongate tubular member 72 by suitable means such as by bending said other end to extend through a pair of retaining slots 116 in the flexible elongate tubular member 72 and being retained therein by the sleeve 91 as shown in FIG. 6. The conductive means for supplying electrical energy to the steering means in the form of the Nitinol wire 111 is provided by the insulated stainless steel core wire or mandrel 78 serving as one of the insulated conductors and the hypotube forming the flexible elongate tubular member 72 serving as the other conductor. Alternatively, first and second insulated conductive wires can be provided within the balloon inflation lumen 76 to provide such conductive means.

An adhesive 121 bonds the coil 101 to core wire or mandrel 78 and a polymer 122 such as silicone fills the space between the adhesive 121 and the ball 102.

The proximal extremity of the catheter 71 shown in FIG. 6 and 7 is constructed in a manner very similar to that shown in the previous embodiment and therefore will not be described in detail.

The operation and use of the balloon-on-a-wire catheter as shown in FIGS. 5 and 6 is substantially identical to that described in connection with the previous embodiment.

It is apparent from the foregoing that there has been provided a low profile balloon-on-a-wire catheter which can be converted from a catheter to a guide wire so that additional conventional balloon catheters can be introduced over the balloon-on-a-wire catheter utilizing the catheter as a stand-alone guide wire. The conversion from a catheter to a guide wire can be readily accomplished merely by removing the attachments provided on the proximal extremity of the catheter, namely the attachment for inflating and deflating the balloon and the connector for making electrical connections to the electrical steering means. The catheter or guide wire is one which when converted can be utilized with rapid exchange catheters.

We claim:

1. A low profile balloon-on-a-wire catheter and/or guide wire comprising a flexible elongate tubular member having proximal and distal extremities and having an outer cylindrical surface and a lumen within the outer cylindrical surface extending from the proximal extremity to the distal extremity, an inflatable balloon carried by the distal extremity of the flexible elongate tubular member, means carried by the flexible elongate tubular member for establishing communication between the lumen and the interior of the inflatable balloon, inflation means removably secured to the proximal extremity of the outer cylindrical surface of the flexible elongate tubular member for supplying an inflation fluid to the lumen for inflating and deflating the balloon, said removable inflation means including means forming a high-pressure seal with the proximal extremity of the flexible elongate tubular member, said removable inflation means when removed providing a proximal extremity of the outer cylindrical surface of the flexible elongate tubular member which is free of obstructions so that a balloon catheter can be advanced over the proximal extremity of the flexible elongate tubular member, steerable means carried by the distal extremity, conductive means connected to the steerable means and extending to the proximal extremity and an electrical connector removably connected to the conductive means at the proximal extremity of the flexible elongate tubular member, said conductive means when removed providing a proximal extremity which is free of obstructions so that a balloon catheter can be advanced over the proximal extremity of the flexible elongate tubular member.

2. A catheter as in claim 1 together with a core wire disposed within the flexible elongate tubular member and extending from the proximal extremity to the distal extremity.

3. A catheter as in claim 2 together with an additional flexible elongate tubular member extending over the core wire and wherein the lumen extending between the first named flexible elongate tubular member and the additional flexible elongate tubular member in communication with the balloon.

4. A catheter as in claim 2 wherein said flexible elongate tubular member is a stainless steel tubular member and wherein said lumen is disposed between the core wire and the interior of the stainless steel tubular member.

5. A catheter as in claim 1 wherein said inflation means removably secured to the proximal extremity of the flexible elongate tubular member includes an entrance port extending through the outer cylindrical surface, means for establishing communication between the entrance port and the lumen in the flexible elongate tubular member, seal means disposed on opposite sides of the entrance port and engaging the flexible elongate tubular member to form a fluid-tight seal therewith but permitting axial movement of the catheter or guide wire.

6. A catheter as in claim 1 together with control means connected to the electrical connector on the proximal extremity for steering the distal extremity of the device.

* * * * *

UNITED STATES PATENT AND TRADEMARK OFFICE
Certificate

Patent No. 5,520,645　　　　　　　　　　　　　　　　　　　　　　　　　Patented: May 28, 1996

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Mir A. Imran, Palo Alto, CA; Cecily M. Hillsman, San Jose, CA; Deepak R. Gandhi, San Jose, CA; Dennis L. Brooks, Santa Clara, CA.

Signed and Sealed this Eighteenth Day of April, 2000.

CORRINE M. MCDERMOTT
*Acting Supervisory Patent Examiner,*
Art Unit 3762